(12) United States Patent
Wu et al.

(10) Patent No.: US 9,897,620 B2
(45) Date of Patent: Feb. 20, 2018

(54) GAS DETECTION DEVICE AND GAS INLET MODULE THEREOF

(71) Applicant: HTC CORPORATION, Taoyuan (TW)

(72) Inventors: Chung-Ju Wu, Taoyuan (TW); Sheng-Chieh Lin, Taoyuan (TW); Yao-Ting Tseng, Taoyuan (TW); Pin-Chung Sun, Taoyuan (TW); Chien-Lung Huang, Taoyuan (TW)

(73) Assignee: HTC CORPORATION, Taoyuan (TW)

( * ) Notice: Subject to any disclaimer, the term of this patent is extended or adjusted under 35 U.S.C. 154(b) by 118 days.

(21) Appl. No.: 14/599,209

(22) Filed: Jan. 16, 2015

(65) Prior Publication Data
US 2016/0209436 A1    Jul. 21, 2016

(51) Int. Cl.
| G01K 15/00 | (2006.01) |
| G01N 33/00 | (2006.01) |
| G01N 33/98 | (2006.01) |
| G01N 33/497 | (2006.01) |

(52) U.S. Cl.
CPC ........... *G01N 33/98* (2013.01); *G01N 33/497* (2013.01)

(58) Field of Classification Search
CPC ....... G01N 33/98; G01N 33/497; A61B 5/097
USPC ............................................................. 73/23
See application file for complete search history.

(56) References Cited

U.S. PATENT DOCUMENTS

| 4,448,058 A * | 5/1984 | Jaffe ...................... A61B 5/091 600/549 |
| 8,443,842 B2 * | 5/2013 | Sonnenberg ............ F15D 1/001 138/40 |
| 2004/0000843 A1 * | 1/2004 | East ...................... F04B 43/046 310/331 |
| 2008/0038207 A1 * | 2/2008 | Edwards ................ A61B 5/097 424/44 |
| 2008/0056946 A1 * | 3/2008 | Ahmad .................. A61B 5/097 422/68.1 |
| 2013/0168548 A1 * | 7/2013 | Wang ..................... A61B 5/082 250/288 |
| 2014/0024130 A1 * | 1/2014 | Marin ................ G01N 33/4972 436/131 |

(Continued)

FOREIGN PATENT DOCUMENTS

| CN | 201083741 Y | 7/2008 |
| TW | 201105946 A1 | 2/2011 |
| WO | WO 2014/116604 A1 | 7/2014 |

*Primary Examiner* — Natalie Huls
*Assistant Examiner* — Monica S Young
(74) *Attorney, Agent, or Firm* — Birch, Stewart, Kolasch & Birch, LLP (57) ABSTRACT

A gas detection device and a gas inlet module thereof are provided. The gas detection device includes a case, a flow disturbing element, a check film and a detector. The case includes a cavity and an exhaust hole. The flow disturbing element is for making a to-be-measured gas vertically enter the cavity. The check film is connected to the flow disturbing element for make the vertical to-be-measured gas flow into the cavity in one-way. The detector is disposed within the cavity and positioned between the exhaust hole and the check film for detecting a property of the to-be-measured gas. The exhaust hole is for making the to-be-measured gas be exhausted.

19 Claims, 8 Drawing Sheets

(56) References Cited

U.S. PATENT DOCUMENTS

| | | | |
|---|---|---|---|
| 2014/0034492 A1* | 2/2014 | Fodor | G01N 27/4078 204/403.01 |
| 2014/0276100 A1* | 9/2014 | Satterfield | A61B 5/082 600/476 |
| 2014/0288454 A1* | 9/2014 | Paz | A61B 5/4845 600/532 |
| 2015/0011906 A1* | 1/2015 | Wallach | A61K 36/00 600/538 |
| 2015/0362478 A1* | 12/2015 | Phillips | A61B 5/082 73/23.3 |
| 2016/0120441 A1* | 5/2016 | Zhu | A61B 5/097 600/538 |
| 2016/0146780 A1* | 5/2016 | Granstam | G01N 33/98 73/23.3 |

* cited by examiner

GAS DETECTION DEVICE AND GAS INLET MODULE THEREOF

TECHNICAL FIELD

The disclosure relates in general to a gas detection device and a gas inlet module thereof, and more particularly to a gas detection device capable of detecting a property of a gas and a gas inlet module thereof.

BACKGROUND

Conventional gas detection device includes a blowing tube and a flow meter. User exhales a gas through the gas tube. The flow of the gas may be measured by the flow meter. However, the conventional gas detection device only can measure the flow of the gas, and accordingly the application of the conventional gas detection device is limited.

Therefore, how to broaden the application of the conventional gas detection device has become a prominent task for the industries.

SUMMARY

The invention is directed to a gas detection device capable of detecting a property of a gas and a gas inlet module thereof.

According to one embodiment of the invention, a gas detection device is provided. The gas detection device includes a case, a flow disturbing element, a check film and a detector. The case includes a cavity and an exhaust hole. The flow disturbing element is used for making a to-be-measured gas uniformly enter the cavity. The check film connects to the flow disturbing element and is used for making the vertical to-be-measured gas flow into the cavity in one-way. The detector is disposed within the cavity and located between the exhaust hole and the check film for detecting a property of the to-be-measured gas. The exhaust hole is for making the to-be-measured gas be exhausted.

According to another embodiment of the invention, a gas detection device is provided. The gas detection device includes a case, a gas inlet module and a detector. The case includes a cavity and an exhaust hole. The gas inlet module is replaceably disposed on the case and interconnects with the cavity, wherein the gas inlet module includes a flow disturbing element and a check film. The flow disturbing element is sued for making a to-be-measured gas vertically enter the cavity. The check film connects to the flow disturbing element and is used for making the vertical to-be-measured gas flow into the cavity in one-way. The detector is disposed within the cavity and located between the exhaust hole and the check film for detecting a property of the to-be-measured gas. The exhaust hole is for making the to-be-measured gas be exhausted.

According to another embodiment of the invention, a gas inlet module is provided. The gas inlet module is replaceably disposed on a case and interconnecting with a cavity of the case, wherein the gas inlet module includes a flow disturbing element and a check film. The flow disturbing element is used for making a to-be-measured gas vertically enter the cavity. The check film connects to the flow disturbing element and is used for making the to-be-measured gas flow into the cavity in one-way.

The above and other aspects of the invention will become better understood with regard to the following detailed description of the preferred but non-limiting embodiment (s). The following description is made with reference to the accompanying drawings.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 1A:
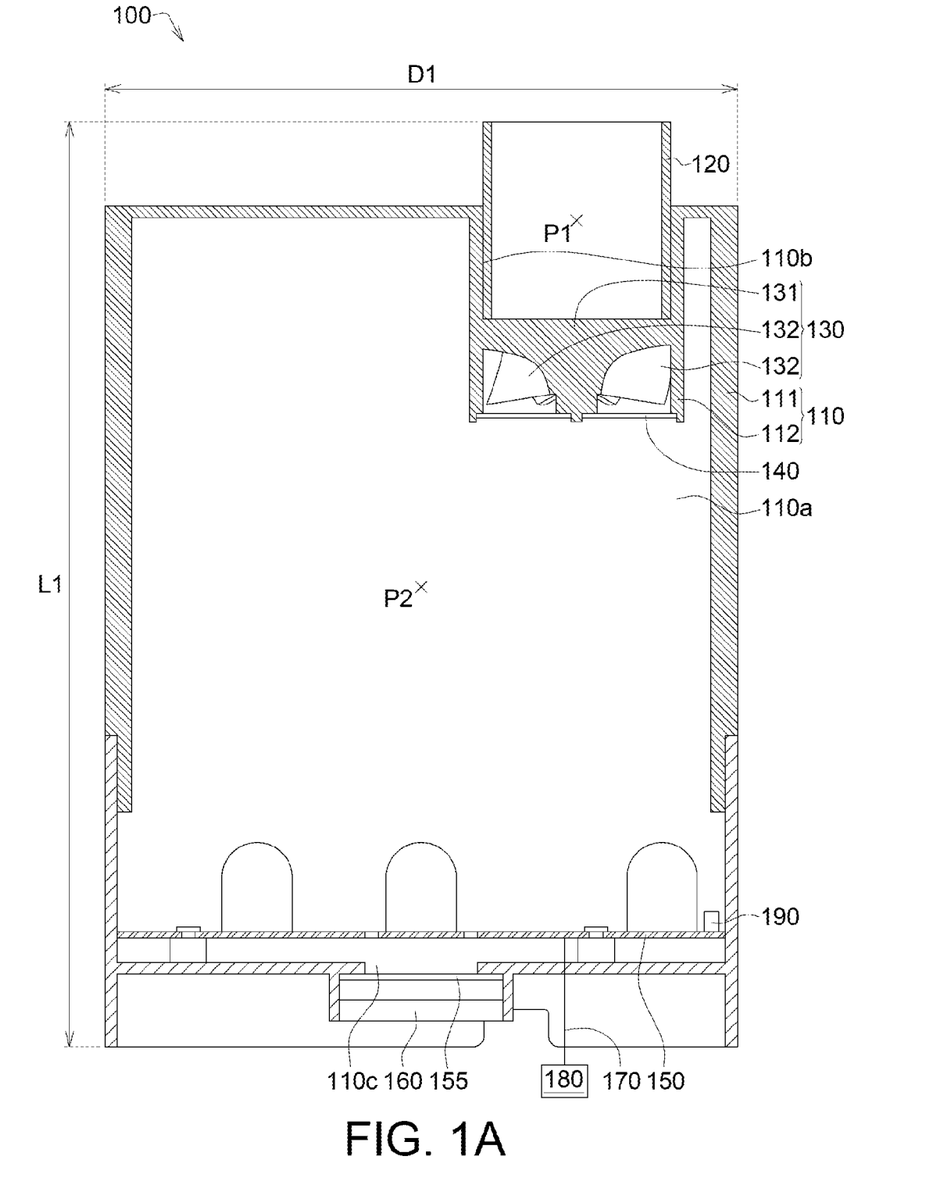
FIG. 1A shows a cross-sectional view of a gas detection device according to an embodiment of the invention.
Figure 1B:
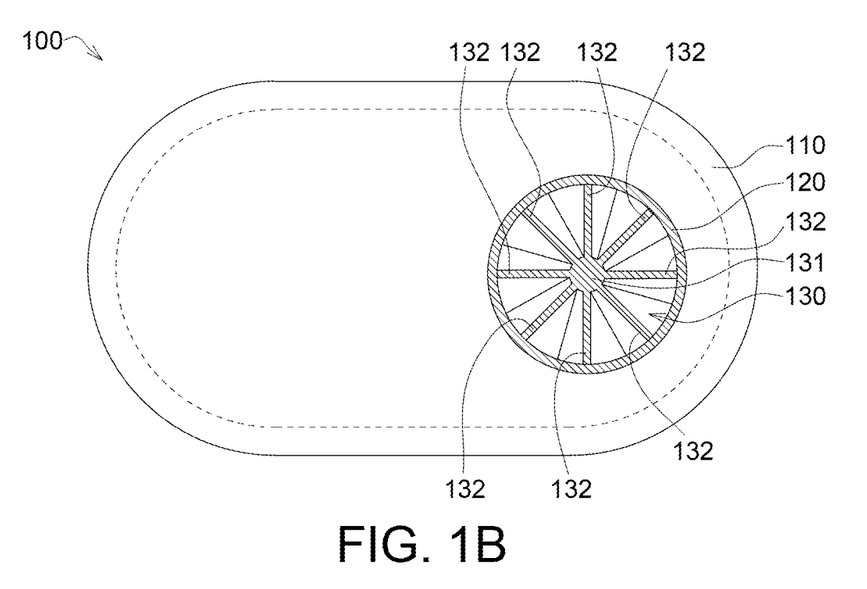
FIG. 1B shows a top view of the gas detection device of FIG. 1A.

Refer to FIGS. 1A and 1B. FIG. 1A shows a cross-sectional view of a gas detection device according to an embodiment of the invention. FIG. 1B shows a top view of the gas detection device of FIG. 1A. The gas detection device 100 is a miniaturization gas detection device and possesses portable property. In an embodiment, the gas detection device 100 has an outer diameter D1 ranging between 50 millimeter and 80 millimeter and has a length L1 ranging between 90 millimeter and 120 millimeter, and accordingly the gas detection device 100 may comply with the requirement of miniaturization.

The gas detection device 100 may detect a property of a gas, such as alcohol concentration of the gas from human or combination of the to-be-measured gas. The gas detection device 100 includes a case 110, a blowing tube 120, a flow disturbing element 130, a check film 140, a detector 150, a filter 155, a forced exhaust element 160, a conductive wire 170, a battery 180 and a wireless transceiver 190.

The case 110 includes an outer casing 111 and an inner casing 112, wherein the inner casing 112 is disposed inside the outer casing 111. The outer casing 111 has a cavity 110a and an exhaust hole 110c, and the inner casing 112 has a recess 110b. The cavity 110a, the recess 110b and the exhaust hole 110c are interconnected with each other. In addition, the case 110 may be made of a material including a plastic, metal or rubber, etc.

The blowing tube 120 may be replaceably disposed on the recess 110b of the inner casing 112. In an embodiment, the blowing tube 120 has an outer diameter slightly larger than an inner diameter of the recess 110b. As a result, after a force is slightly applied to the blowing tube 120, the blowing tube 120 may be detached from the recess 110b or be mounted on the recess 110b. Due to the blowing tube 120 possessing replaceable property, the blowing tube 120 becomes a disposable blowing tube. In detail, after the blowing tube 120 is detached from the recess 110b, the blowing tube 120 may be thrown off. Next gas detection may be performed after a new blowing tube 120 is mounted on the recess 110b.

User may exhale the to-be-measured gas G1 (shown in FIG. 2) into the cavity 110a for detecting the property of the to-be-measured gas G1. In the present embodiment, the cavity 110a of the outer casing 111 and the recess 110b of the inner casing 112 may be interconnected with each other, and accordingly a flowing distance of the to-be-measured gas G1 between the blowing tube 120 to the cavity 110a may be shorted, and any physical tube between the blowing tube 120 to the cavity 110a may be omitted.

As shown in FIGS. 1A and 1B, the flow disturbing element 130 is located within the recess 110b. The flow disturbing element 130 includes a central pillar 131 and a plurality of disturbing blades 132 each extending to an inner wall of the recess 110b from the central pillar 131. In the present embodiment, the number of the disturbing blades 132 is eight. In another embodiment, the number of the disturbing blades 132 may be more than eight or less than eight. In the present embodiment, the case 110 and the flow disturbing element 130 may be formed into single piece. For example, the case 110 and the flow disturbing element 130 may be formed by using a plastic injection manufacturing process. In another embodiment, the case 110 and the flow disturbing element 130 may be formed separately, and then combined by using a temporary way or a permanent way, wherein the temporary way is such as engaging, screwing, and the permanent way is such as adhering, welding or riveting. The flow disturbing element 130 may be made of a material including plastic, metal or rubber, etc. When the case 100 and the flow disturbing element 130 are integrated into single piece, the flow disturbing element 130 may be made of the same material as that of the case 110. When the case 100 and the flow disturbing element 130 are formed separately, the flow disturbing element 130 may be made of a different material from that of the case 110.

As shown in FIG. 1A, since the to-be-measured gas G1 has not been exhaled yet, the pressure P1 of the blowing tube 120 is substantially equal to the pressure P2 of the cavity 110a.

Figure 2:
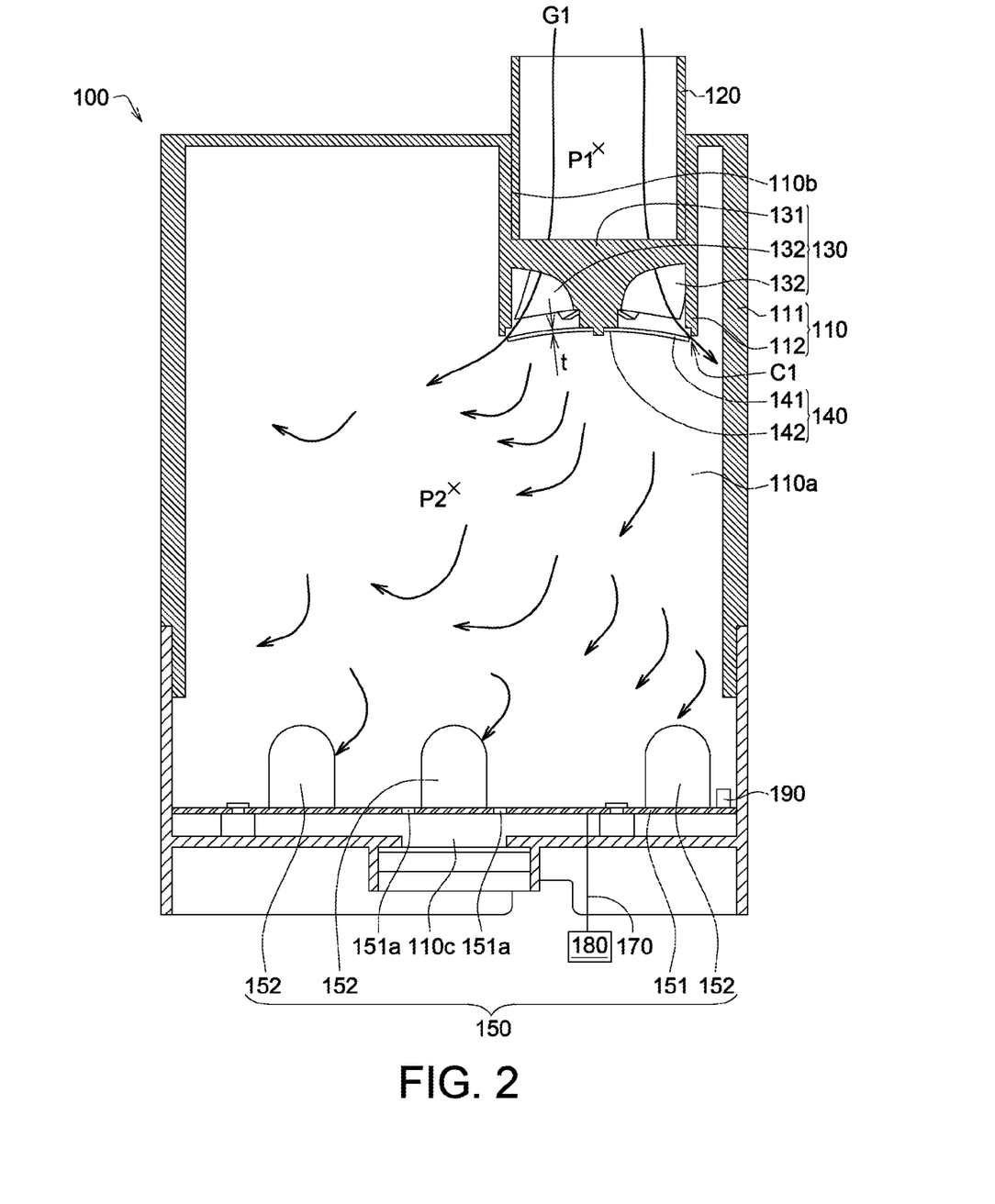
FIG. 2 shows a diagram of the to-be-measured gas entering the gas detection device of FIG. 1A.

FIG. 2 shows a diagram of the to-be-measured gas entering the gas detection device of FIG. 1A. When detecting the to-be-measured gas G1, user may exhale the to-be-measured gas G1 through the blowing tube 120. At this time, the pressure P1 of the blowing tube 120 is larger than the pressure P2 of the cavity 110a, such that a pushing force toward the cavity 110a is applied to the check film 140 and the check film 140 is forced to expose a gas channel C1 for making the to-be-measured gas G1 enter the cavity 110a through the gas channel C1.

A center 142 of the check film 140 is fixed to the central pillar 131, and an edge of 141 of the check film 140 is movable with respect to the center 142 (is deemed a free end). Since the disturbing blade 132 is a spiral shape, the to-be-measured gas G1 generates vertical motion and flows away from the center 142 through the disturbing blade 132, such that the to-be-measured gas G1 pushed the edge 141 of the check film 140. Due to a long force arm from the center 142 to the edge 141, the to-be-measured gas G1 pushes the check film 140 labor-savingly, and accordingly the gas channel C1 is easy to be exposed between the edge 141 of the check film 140 and the inner casing 112. In an embodiment, the check film 140 is an airproof film (without pores), and accordingly the to-be-measured gas G1 is prevented from being escaping to the cavity 110a through the check film 140 itself. As a result, the to-be-measured gas G1 also can push the edge 141 of the check film 140 to expose the gas channel C1 by a larger force (if the escaping occurs, the pushing force become less).

In addition, since the to-be-measured gas G1 vertically enters the cavity 110a and accordingly may uniformly is distributed over the whole cavity 110a, and the to-be-measured gas G1 may rapidly reach the detector 150 for being detected or analyzed by the detector 150. In an embodiment, the check film 140 may be transparent film, translucent film or opaque film. In an embodiment, the check film 140 has a thickness t1 ranging between 45 micrometer and 55 micrometer. In another embodiment, the thickness t1 may be less than 45 micrometer or larger than 55 micrometer. In addition, the check film 140 may be shaped into circle shape, rectangular shape or elliptical shape.

In an embodiment, the check film 140 may be made of a material including polyethylene, polytetrafluoroethylene, polyester or a combination thereof. In addition, the check film 140 may be a single-layered structure or a multi-layered structure. In terms of the multi-layered structure, each layer of the check film 140 may be made of any of the material as described above-mentioned or a combination thereof.

The detector 150 is disposed within the cavity 110a and between the exhaust hole 110c and the check film 140 for detecting the property of the to-be-measured gas G1. The detector 150 includes a circuit board 151 and at least one gas property detector 152. The circuit board 151 has at least one through hole 151a. The gas property detector 152 is disposed on the circuit board 151 and faces the cavity 110a for detecting for analyzing the property of the to-be-measured gas G1. In addition, in another embodiment, the detector 150 also may be flow meter.

Figure 6:
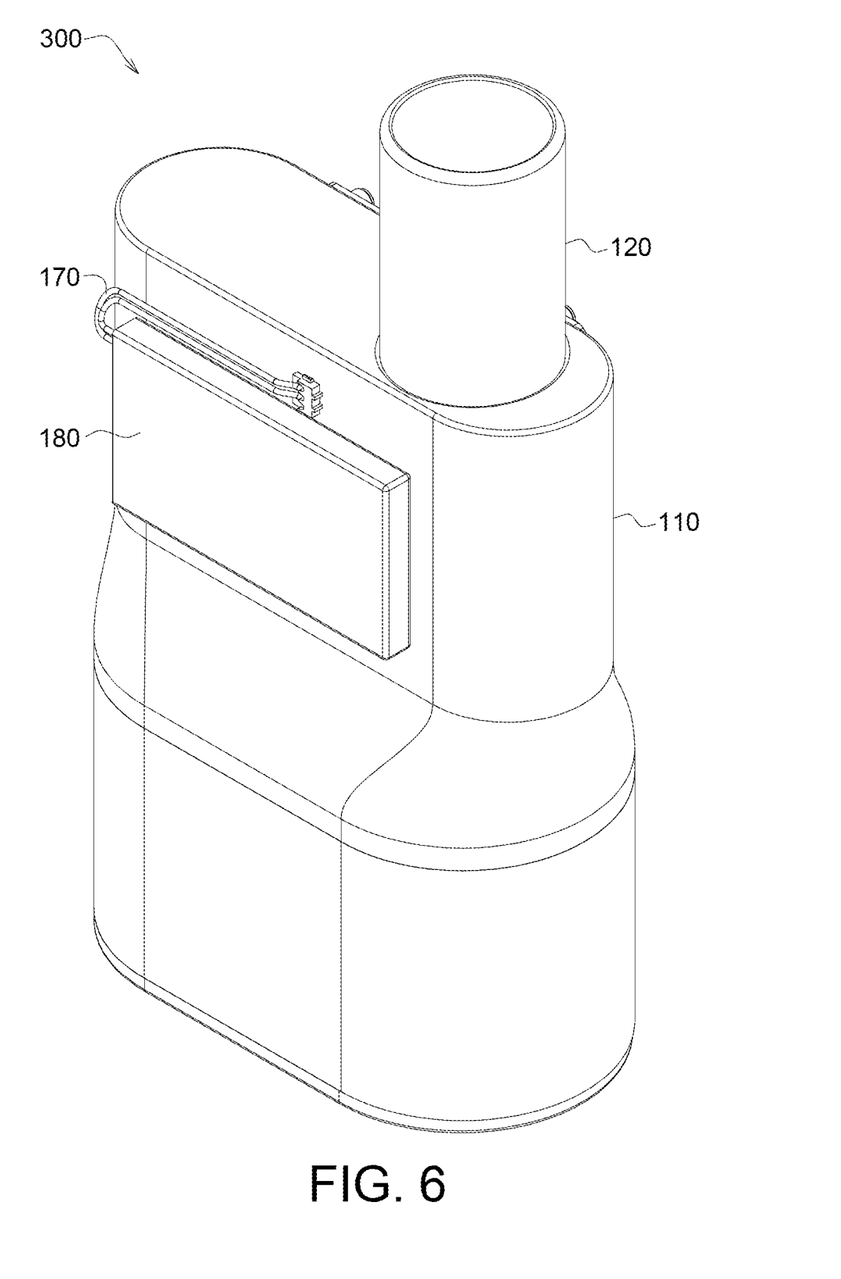
FIG. 6 shows an appearance view of a gas detection device according to another embodiment of the invention.

In the present embodiment, the conductive wire 170 may connect the circuit board 151 and the battery 180, such that the battery 180 may provide the circuit board 151 with power, wherein the configuration of the battery 180 is shown in FIG. 6. The wireless transceiver 190 may transmit an analysis result of the to-be-measured gas G1 to an exterior receiver (not shown) by using wireless communication technique, wherein the exterior receiver is computer, cell-phone or server, for example. In another embodiment, although not shown, the gas detection device 100 may further include a transmission wire connecting the circuit board 151 and the exterior receiver, such that the analysis result of the to-be-measured gas G1 may be transmitted to the exterior receiver through the transmission wire.

Figure 3:
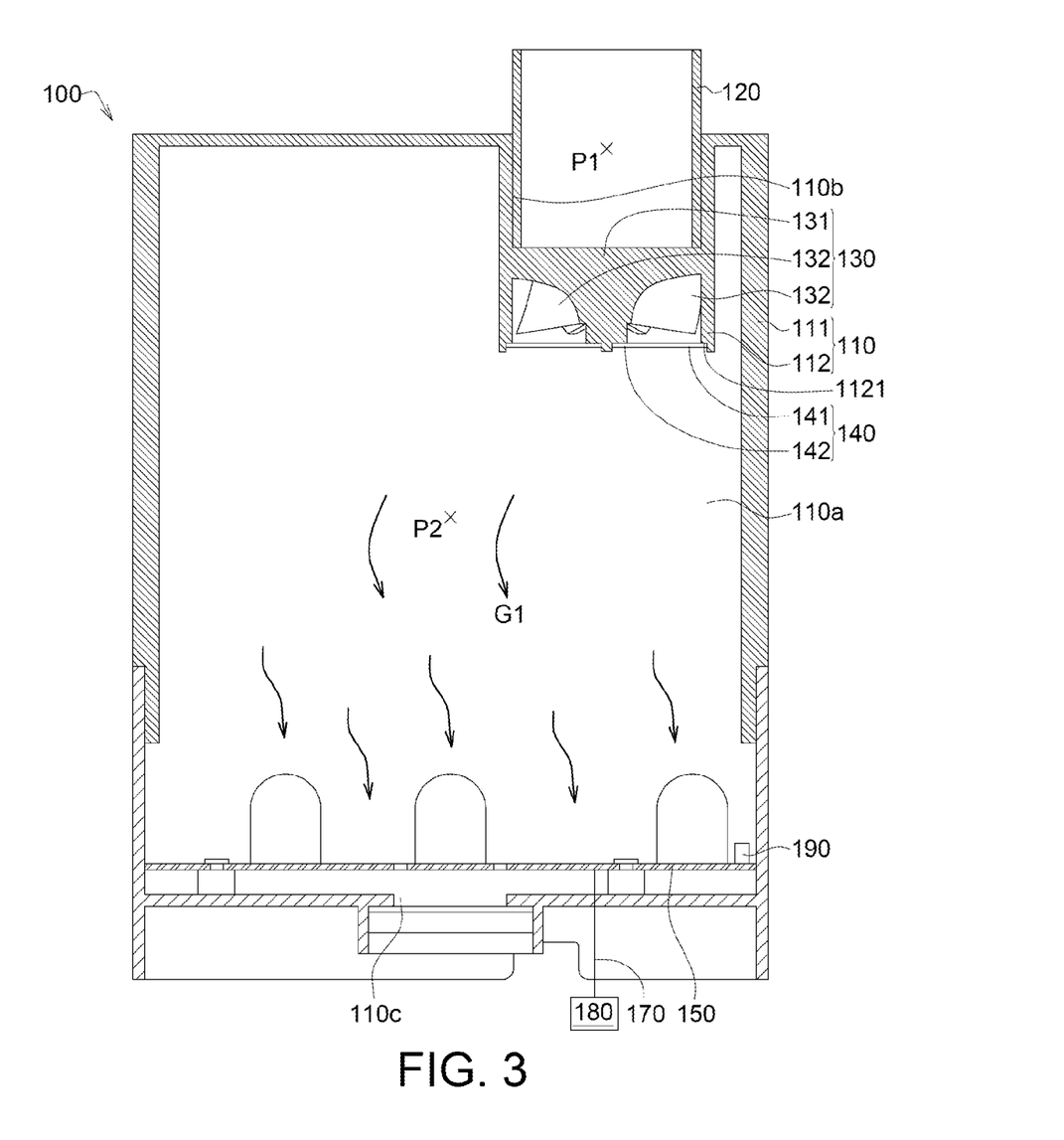
FIG. 3 shows a diagram of the detector of FIG. 2 detecting the to-be-measured gas.

FIG. 3 shows a diagram of the detector of FIG. 2 detecting the to-be-measured gas. As shown in FIG. 3, when the to-be-measured gas G1 is exhaled into the cavity 110a, the pressure P2 of the cavity 110a becomes larger than the pressure P1 of the blowing tube 120 due to the cavity 110a is filled with the to-be-measured gas G1, such that the edge 141 of the check film 140 is pushed toward the blowing tube 120 to close the gas channel C1 (as shown in FIG. 2), and accordingly the to-be-measured gas G1 within the cavity 110a may be prevented from flowing back the blowing tube 120. In detail, the to-be-measured gas G1 only enters the cavity 110a in one-way and can't flow back the blowing tube 120 through the check film 140.

In an embodiment, the check film 140 is an airproof film, that is, the check film 140 has no pore. Thus, when the gas channel C1 of FIG. 2 is closed, the to-be-measured gas G1 within the cavity 110a may be prevented from flowing back the blowing tube 120 through the material of the check film 140 itself. In addition, the inner casing 112 includes a ring-shaped block wall 1121, and the edge 141 of the check film 140 may be selectively blocked by the block wall 1121.

As shown in FIG. 3, since the pressure P2 of the cavity 110a is larger than the pressure P1 of the blowing tube 120, a pressure toward the blowing tube 120 is applied to the check film 140, and accordingly the check film may firmly presses on the block wall 1121. As a result, the to-be-measured gas G1 within the cavity 110a is difficult to flow back the blowing tube 120 through the connecting portion between the check film 140 and the block wall 1121.

Figure 4A:
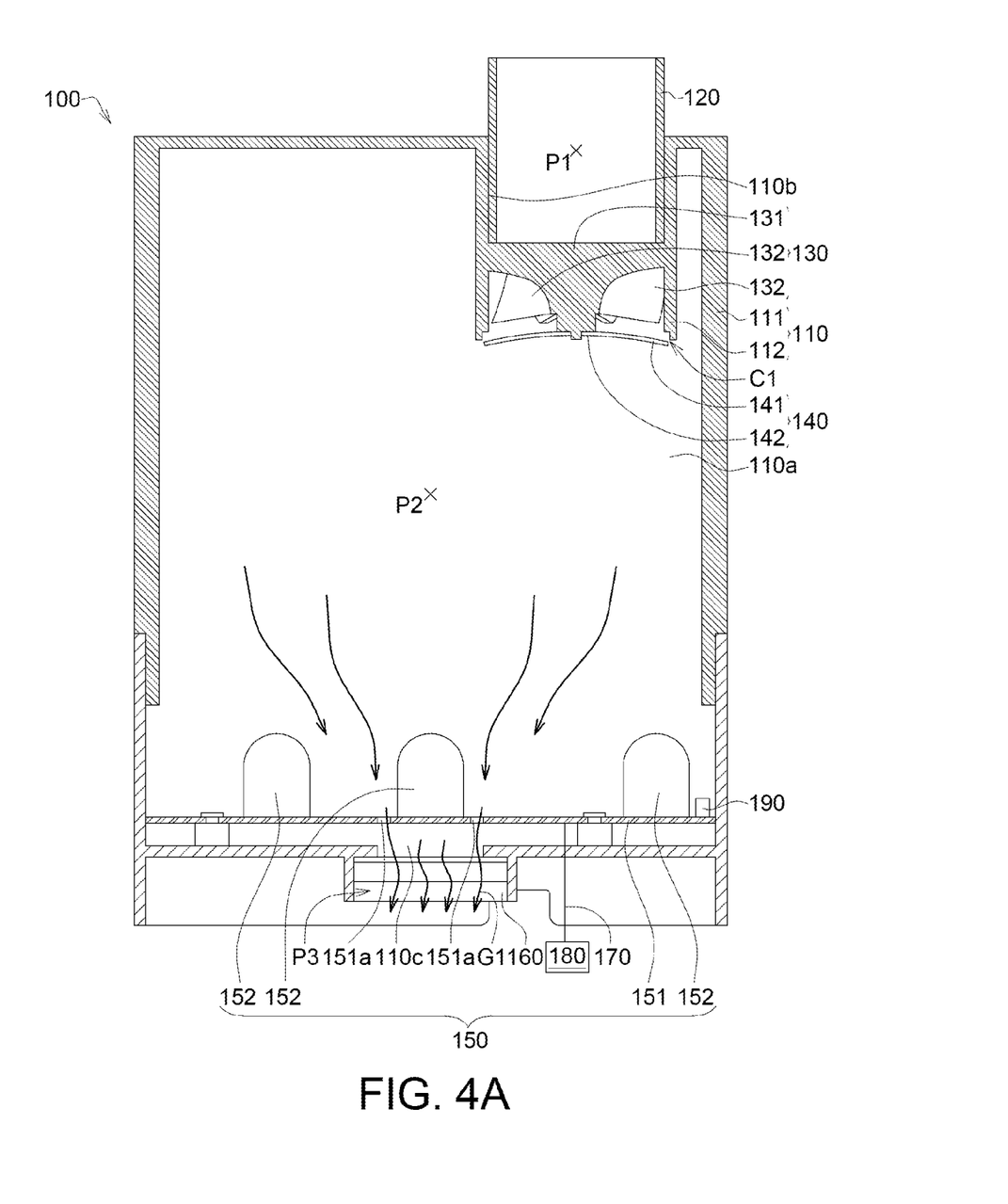
FIG. 4A shows a diagram of the to-be-measured gas of FIG. 3 being forcedly exhausted.
Figure 4B:
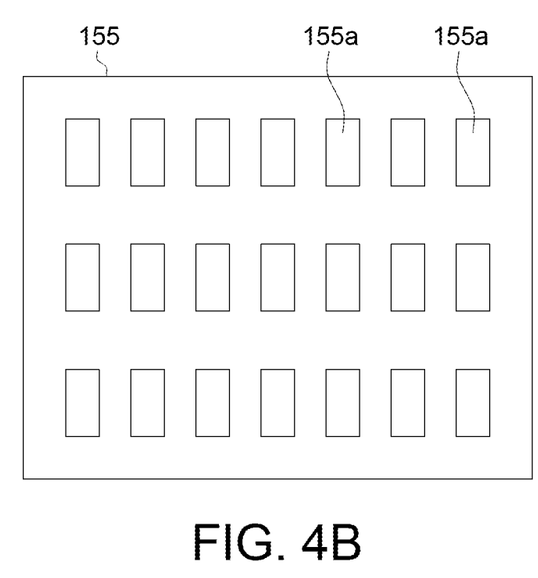
FIG. 4B shows a top view of the filter of FIG. 4A.

Referring FIGS. 4A and 4B, FIG. 4A shows a diagram of the to-be-measured gas of FIG. 3 being forcedly exhausted, and FIG. 4B shows a top view of the filter of FIG. 4A. After the detection is finished, the forced exhaust element 160 may exhaust the to-be-measured gas G1 outside the gas detection device 100, and accordingly a negative effect of the residual to-be-measured gas G1 on the next exhaled to-be-measured gas G1 may be prevented, and the analysis accuracy of the next exhaled to-be-measured gas G1 may be promoted. When the forced exhaust element 160 operates, the pressure P2 of the cavity 110a becomes larger than the pressure P3 of the exterior of the cavity 110a, such that the to-be-measured gas G1 may be exhausted outside the cavity 110a. In addition, as shown FIG. 4A, under the circumstance of increasing the exhausting power of the forced exhaust element 160, for example, the rotational speed is increased, the pressure P1 of the blowing tube 120 becomes larger than the pressure P3 of the exterior of the cavity 110a, and accordingly the gas channel C1 between the edge 141 of the check film 140 and the inner casing 112 may be exposed. As a result, the residual to-be-measured gas G1 within the flow disturbing element 130 also may be exhausted outside the cavity 110a, and accordingly a negative effect of the residual to-be-measured gas G1 within the flow disturbing element 130 on the next exhaled to-be-measured gas G1 may be prevented, and the analysis accuracy of the next exhaled to-be-measured gas G1 may be promoted. Whether the gas channel C1 is exposed depends on practical situation, and, such exemplification is not meant to be for limiting. That is, in another embodiment, the gas channel C1 also may not be exposed.

As shown in FIG. 4A, since the circuit board 151 has the through hole 151a, the to-be-measured gas G1 may be exhausted outside the gas detection device 100 through the through hole 151a and the exhaust hole 110c when the forced exhaust element 160 operates. In an embodiment, the forced exhaust element 160 is, for example, a fan, Although not shown in figure, the conductive wire 170 also may connect the forced exhaust element 160 and the battery 180, such that the battery 180 may provide the forced exhaust element 160 with power for operating the forced exhaust element 160.

As shown in FIG. 4B, the filter 155 has at least one through hole 155a, such that the to-be-measured gas G1 within the cavity 110a may be exhausted outside the gas detection device 100 through the through hole 151a, the exhaust hole 110c and the through hole 155a of the filter 155 when the forced exhaust element 160 operates. The through hole 155a has an inner diameter smaller than an inner diameter of the exhaust hole 110c. Due the design of the filter 155, the exterior particles may be prevented from entering the cavity 110a through the exhaust hole 110c.

Despite the replaceable element of the gas detection device 100 of the present embodiment of the invention is exemplified by the blowing tube 120, however, such exemplification is not meant to be for limiting.

Figure 5:
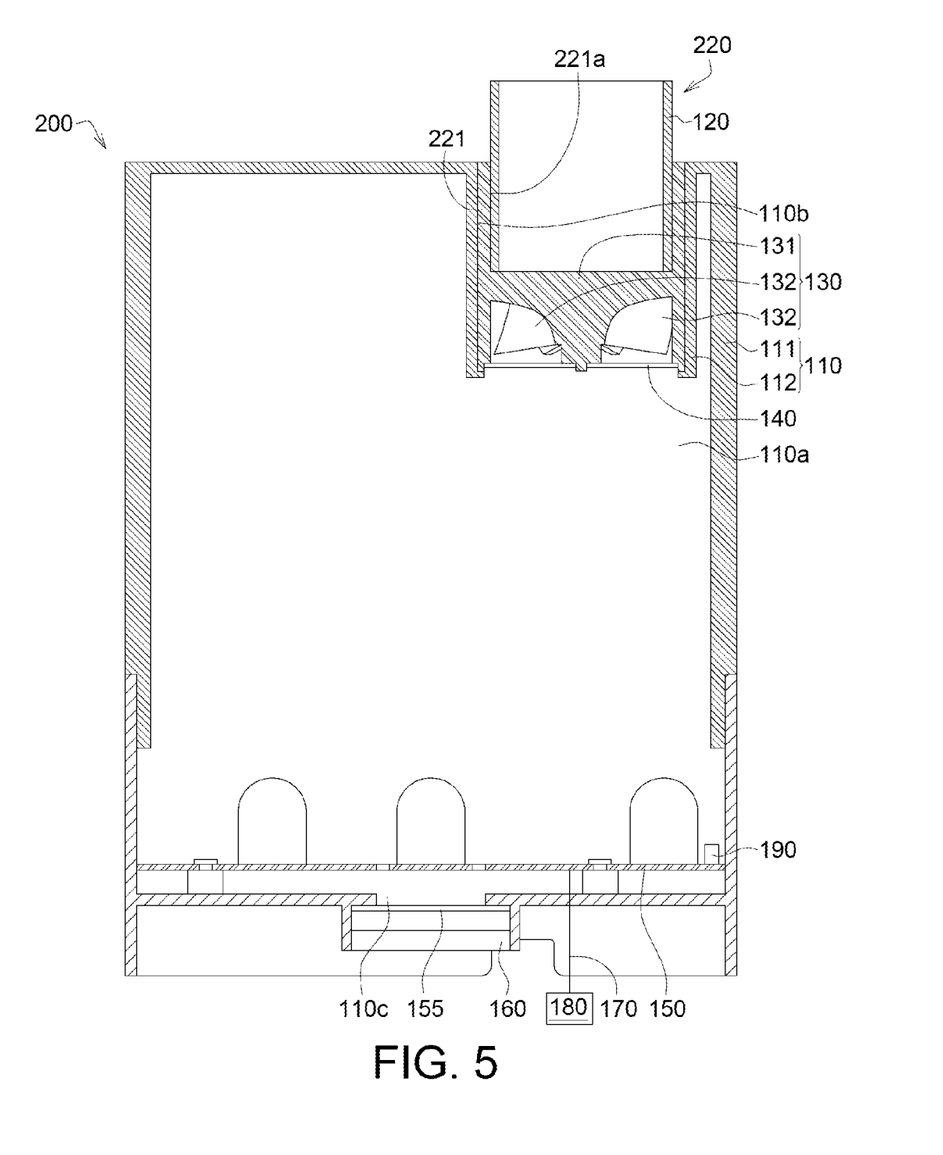
FIG. 5 shows a cross-sectional view of a gas detection device according to another embodiment of the invention.

FIG. 5 shows a cross-sectional view of a gas detection device 200 according to another embodiment of the invention. The gas detection device 200 includes the casing 110, a gas inlet module 220, the detector 150, the filter 155, the forced exhaust element 160, the conductive wire 170, the battery 180 and the wireless transceiver 190. The casing 110 includes the outer casing 111 and the inner casing 112, wherein the inner casing 112 connects with and is located within the outer casing 111. The inner casing 112 has the recess 110b, and the gas inlet module 220 may be replaceably disposed within the recess 110b of the inner casing 112. Compared with the gas detection device 100, the replaceable element of the gas detection device 200 is the entire gas inlet module 220.

The gas inlet module 220 includes a case 221, the blowing tube 120, the flow disturbing element 130 and the check film 140. The case 221 has a recess 221a, the flow disturbing element 130 is fixed within the recess 221a. In detail, the flow disturbing element 130 includes the central pillar 131 and several disturbing blades 132 each extending to the inner sidewall of the recess 221a from the central pillar 131. In the present embodiment, the blowing tube 120 is replaceably mounted within the recess 221a. In another embodiment, the gas inlet module 220 and the case 221 may be integrated into single piece. For example, the blowing tube 120 and the case 221 of the gas inlet module 220 may be integrated into single piece by using injection molding.

In an embodiment, the case 221 of the gas inlet module 220 has an outer diameter slightly larger than an inner diameter of the cavity 110a of the inner casing 112. As a result, after the force is slightly applied, the whole gas inlet module 220 may be detached from or mounted on the recess 110b. Since the gas inlet module 220 has replaceability, the gas inlet module 220 becomes a disposable gas inlet module. In detail, after the gas inlet module 220 is detached from the recess 110b, the gas inlet module 220 may be thrown off. In next gas detection, a new gas inlet module 220 may be mounted on the recess 110b for detecting gas.

FIG. 6 shows an appearance view of a gas detection device 300 according to another embodiment of the invention. The gas detection device 300 includes the casing 110, the gas inlet module 120, the flow disturbing element 130 (not shown), the check film 140 (not shown), the detector 150 (not shown), the filter 155 (not shown), the forced exhaust element 160 (not shown), the conductive wire 170, the battery 180 and the wireless transceiver 190 (not shown). As shown in FIG. 6, the battery 180 may be disposed outside the case 110, and the conductive wire 170 connects with the detector 150 (not shown) for providing the detector 150 with power. In another embodiment, the battery 180 is also disposed inside the case 110.

In addition, the configuration of the battery 180 and the conductive wire 170 of the gas detection device 100 and 200 as stated above may be similar to the configuration of the battery 180 and the conductive wire 170 of the gas detection device 300, and the similarity is not repeated.

To summarize, the gas detection device and the gas inlet module thereof disclosed in above embodiments of the invention at least provide have following effects:

(1). In an embodiment, the gas detection device is a miniaturization gas detection device, and thus possesses portable property.

(2). In an embodiment, the gas detection device includes the replaceable blowing tube. As a result, it is convenient to replace the blowing tube.

(3). In an embodiment, the gas detection device includes the flow disturbing element. The flow disturbing element makes the to-be-measured gas generate vertical motion, such that the to-be-measured gas rapidly reaches the detector and thus the required detecting time may be reduced.

(4). In an embodiment, the gas detection device includes the forced exhaust element. The forced exhaust element may rapidly exhaust the to-be-measured gas within the case outside the case, and most or almost all of the to-be-measured gas may be exhausted outside the case for the next gas detection.

(5). In an embodiment, the gas detection device includes the check film. The check film connects with the flow disturbing element and is used for making the to-be-measured gas flow into the cavity in one-way.

(6). In an embodiment, the flow disturbing element and the check film may integrated into the gas inlet module, such that the flow disturbing element and the check film may be replaced together with the gas inlet module. As a result, the residual to-be-measured gas in the flow disturbing element and the check film may be prevented from affecting the next gas detection.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A gas detection device, comprising:
a case comprising a cavity and an exhaust hole in a bottom of the cavity;
a flow disturbing element for making a to-be-measured gas uniformly enter the cavity;
a check film connecting to the flow disturbing element and used for making the vortical to-be-measured gas flow into the cavity in one-way; and
a detector disposed within the cavity and located between the exhaust hole and the check film for detecting a property of the to-be-measured gas;
wherein the exhaust hole is for making the to-be-measured gas be exhausted,
wherein the detector is disposed on a lower portion of the cavity and comprises a circuit board, and the gas detection device further comprises a wireless transceiver disposed on the circuit board and configured to transmit an analysis result of the to-be-measured gas to an exterior receiver, and
wherein the gas detection device further comprises:
a forced exhaust element disposed outside the cavity for exhausting the to-be-measured gas within the cavity outside the cavity through the exhaust hole.

2. The gas detection device according to claim 1, wherein the circuit board having at least one through hole for making the to-be-measured gas pass through, the detector further comprising:
a gas property detector disposed on the circuit board for detecting the property of the to-be-measured gas.

3. The gas detection device according to claim 1, wherein the case has a recess, and the gas detection device further comprises:
a blowing tube replaceably disposed on the recess.

4. The gas detection device according to claim 3, wherein the flow disturbing element comprises a central pillar and a plurality of disturbing blades each extending to an inner wall of the case from the central pillar.

5. The gas detection device according to claim 4, wherein the case comprises a block wall, a center of the check film is fixed to the central pillar, and an edge of the check film is selectively blocked by the block wall.

6. The gas detection device according to claim 1, wherein the case and the flow disturbing element are formed into single piece.

7. The gas detection device according to claim 1, wherein the gas detection device has an outer diameter and a length, the outer diameter ranges between 50 millimeter and 80 millimeter, and the length ranges between 90 millimeter and 120 millimeter.

8. The gas detection device according to claim 1, wherein a thickness of the check film ranges between 45 micrometer and 55 micrometer.

9. The gas detection device according to claim 1, wherein the check film is made of a material comprising polyethylene, polytetrafluoroethylene, polyester or a combination thereof.

10. The gas detection device according to claim 1, wherein the check film is a single-layered structure or a multi-layered structure.

11. The gas detection device according to claim 1, further comprising:
a battery disposed outside the case; and
a conductive wire connecting the battery and the detector.

12. A gas detection device, comprising:
a case comprising a cavity and an exhaust hole in a bottom of the cavity;
a gas inlet module replaceably disposed on the case and interconnecting with the cavity, wherein the gas inlet module comprises:
a flow disturbing element for making a to-be-measured gas vertically enter the cavity; and
a check film connecting to the flow disturbing element and used for making the vertical to-be-measured gas flow into the cavity in one-way; and
a detector disposed within the cavity and located between the exhaust hole and the check film for detecting a property of the to-be-measured gas;
wherein the exhaust hole is for making the to-be-measured gas be exhausted,
wherein the detector is disposed on a lower portion of the cavity and comprises a circuit board, and the gas detection device further comprises a wireless transceiver disposed on the circuit board and configured to transmit an analysis result of the to-be-measured gas to an exterior receiver, and
wherein the gas detection device farther comprises:
a forced exhaust element disposed outside the cavity for exhausting the to-be-measured gas within the cavity outside the cavity through the exhaust hole.

13. The gas detection device according to claim 12, wherein the flow disturbing element and the case are formed into single piece.

14. The gas detection device according to claim 12, wherein the case has a recess, and the gas detection device further comprises:
a blowing tube replaceably disposed on the recess.

15. A gas inlet module, replaceably disposed on a case and interconnecting with a cavity of the case of a gas detection device, wherein the gas inlet module comprises:
a flow disturbing element for making a to-be-measured gas vertically enter the cavity; and
a check film connecting to the flow disturbing element and used for making the to-be-measured gas flow into the cavity in one-way,
wherein a detector of the gas detection device disposed on a lower portion of the cavity and comprises a circuit board disposed opposite to the gas inlet module, and the gas detection device further comprises a wireless transceiver disposed on the circuit board and configured to transmit an analysis result of the to-be-measured gas to an exterior receiver, and wherein a forced exhaust element of the gas detection device is disposed outside the cavity for exhausting the to-be-measured gas within the cavity outside the cavity.

16. The gas inlet module according to claim 15, further comprises:

a case;

wherein the flow disturbing element is fixed to the case of the gas inlet module.

17. The gas inlet module according to claim 15, wherein the flow disturbing element comprises a central pillar and a plurality of disturbing blades each extending to an inner wall of the case from the central pillar.

18. The gas inlet module according to claim 17, wherein the check film connects with the central pillar.

19. The gas inlet module according to claim 17, wherein the case comprises a block wall, a center of the check film is fixed to the central pillar, and an edge of the check film is selectively blocked by the block wall.

* * * * *